US008463376B2

(12) United States Patent
Curtis

(10) Patent No.: US 8,463,376 B2
(45) Date of Patent: Jun. 11, 2013

(54) SYSTEM AND METHOD FOR TRANSVASCULAR ACTIVATION OF CARDIAC NERVES WITH AUTOMATIC RESTART

(76) Inventor: Guy P. Curtis, San Diego, CA (US)

(*) Notice: Subject to any disclaimer, the term of this patent is extended or adjusted under 35 U.S.C. 154(b) by 49 days.

(21) Appl. No.: 13/155,256

(22) Filed: Jun. 7, 2011

(65) Prior Publication Data

US 2011/0301666 A1    Dec. 8, 2011

Related U.S. Application Data

(63) Continuation-in-part of application No. 12/190,097, filed on Aug. 12, 2008, now abandoned.

(51) Int. Cl.
*A61N 1/00* (2006.01)
(52) U.S. Cl.
USPC ............................................................. 607/2
(58) Field of Classification Search
USPC ................. 607/2, 9, 17, 122, 116, 11
See application file for complete search history.

(56) References Cited

U.S. PATENT DOCUMENTS

| 4,583,553 | A | 4/1986 | Shah et al. |
| 4,993,421 | A | 2/1991 | Thornton |
| 6,934,583 | B2 | 8/2005 | Weinberg et al. |
| 6,937,896 | B1 * | 8/2005 | Kroll ................................. 607/9 |
| 7,096,064 | B2 | 8/2006 | Deno et al. |
| 7,481,759 | B2 | 1/2009 | Whitehurst |
| 7,647,101 | B2 | 1/2010 | Libbus et al. |
| 7,761,151 | B2 | 7/2010 | Pastore et al. |
| 7,792,564 | B2 | 9/2010 | Boese et al. |
| 7,877,142 | B2 | 1/2011 | Moaddeb et al. |
| 2007/0255379 | A1 | 11/2007 | Williams et al. |
| 2007/0299477 | A1 * | 12/2007 | Kleckner et al. ................. 607/9 |
| 2008/0051839 | A1 | 2/2008 | Libbus et al. |
| 2008/0234772 | A1 * | 9/2008 | Shuros et al. ................... 607/11 |
| 2009/0036948 | A1 | 2/2009 | Levin |
| 2010/0042185 | A1 | 2/2010 | Curtis |
| 2010/0152804 | A1 * | 6/2010 | Kleckner et al. ................ 607/17 |

* cited by examiner

*Primary Examiner* — George Manuel
*Assistant Examiner* — Robert N Wieland
(74) *Attorney, Agent, or Firm* — Nydegger and Associates

(57) ABSTRACT

A system and method for electrically stimulating the heart muscle to improve heart function requires identifying a site in the venous system adjacent a sympathetic nerve. An electrode is then positioned at the site to electrically stimulate the nerve. In turn, this stimulation releases norepinephrine from the nerve to improve heart muscle contraction.

20 Claims, 2 Drawing Sheets

SYSTEM AND METHOD FOR TRANSVASCULAR ACTIVATION OF CARDIAC NERVES WITH AUTOMATIC RESTART

This application is a continuation-in-part of application Ser. No. 12/190,097, filed Aug. 12, 2008, which is currently pending. The contents of application Ser. No. 12/190,097 are incorporated herein by reference.

FIELD OF THE INVENTION

The present invention pertains generally to systems and methods for treating heart disease. More particularly, the present invention pertains to systems and methods for electrically stimulating the heart muscle to improve heart function. The present invention is particularly, but not exclusively, useful as a system or method wherein an electrode is positioned in the coronary sinus, or a vein connected with the coronary sinus, to be adjacent a sympathetic nerve for stimulation of the nerve and muscle to improve heart muscle contractions.

BACKGROUND OF THE INVENTION

Normal heart function is characterized by a rhythmic contraction of the heart muscle, wherein each contraction is followed by a refractory period and cardiac diastole during which the heart muscle relaxes to be refilled with circulating blood. A diseased heart, however, may experience filling disorders or ineffective contractions under certain conditions that diminish heart and circulatory function leading to heart failure. In response to a diminished heart function, a relatively common practice has been to place electrodes via the cardiac veins on the epicardial surface of the heart's left ventricle, and to then electrically stimulate the area of placement for the purpose of synchronizing heart contractions. Such a technique, however, is not predictably effective and has resulted in no benefit in significant numbers of patients where substantial benefit would have been predicted. Moreover, the possibility of cell damage in the area of electrode placement from observed loss in contractile function has raised additional concerns.

Though several mechanisms are known to contribute to contractions of the heart muscle, they each do so in different ways. As indicated above, one such mechanism involves a direct electrical stimulation of the heart muscle and control of the sequence of muscle activation. Another mechanism for improving muscle function, however, involves the stimulation of sympathetic nerves. More specifically, it is known that norepinephrine (a derivative of adrenaline released from the nervous system nerve endings at the heart) is a potent stimulant of contraction on the heart muscle. It is also known that sympathetic nerves can be electrically stimulated to secrete norepinephrine in response to relatively low intensity stimulation patterns. Importantly, stimulation of the sympathetic nervous system can be efficacious for energizing the heart muscle by causing the release of norepinephrine at low stimulation intensities that do not have any direct effects to electrically stimulate the heart muscle itself.

In light of the above, it is an object of the present invention to provide a system and method that will improve heart function by indirectly stimulating the sympathetic nervous system. Another object of the present invention is to provide a system and method that avoids direct stimulation of the heart muscle while improving heart function with indirect electrical stimulation. Yet another object of the present invention is to improve heart function using low intensity, electrical stimulation patterns during the heart's refractory period that will not adversely affect the heart muscle, or otherwise diminish its local muscle function. Another object of the present invention is to provide a system and method for improving heart function by electrical stimulation that alters the sequence of muscle activation but is also focused on activation of the cardiac sympathetic nervous system, is simple to implement, is easy to use and is comparatively cost effective.

SUMMARY OF THE INVENTION

In accordance with the present invention, a system and method for electrically stimulating a sympathetic nerve to improve heart function employs an electrode that is positioned in the vasculature of a patient for epicardial heart stimulation. More particularly, the electrode is positioned in the coronary sinus, or in a vein connected to the coronary sinus. And, it is positioned adjacent to a sympathetic nerve (i.e. nerve bundle). Selective stimulation of the sympathetic nerve by the electrode then causes a secretion (release) of norepinephrine that improves the heart muscle contraction (i.e. left ventricle) in the area of the electrode, blood vessel (vein) and nerve.

Structurally, the system of the present invention, includes a voltage source (e.g. a pacemaker), a stimulator, and a sensor that are respectively connected to a deployment catheter. Specifically, the voltage source and stimulator are electrically connected to an electrode that is located at/near the distal end of the deployment catheter. Similarly, the sensor is electrically connected to a probe that is also located at/near the distal end of the deployment catheter. Further, the system can include a computer having pre-programmed instructions for concertedly controlling the operation of the voltage source and the stimulator. As envisioned for the present invention, the voltage source can be either a pacemaker or a pacing catheter of a type well known in the pertinent art. In use, the voltage source (pacemaker) is programmed to establish heart muscle contractions at a predetermined rate. Specifically, this is done to control the desired frequency of heart cycles per minute, and to thereby support a more synchronous activation of cardiac pump function.

As envisioned for the present invention, the stimulator can be incorporated as an additional feature of the voltage source, or it can be used as an independent component. In either case, operations of the voltage source and the stimulator are coordinated by the computer. Thus, in addition to the heart muscle contractions that are stimulated by the voltage source at the predetermined rate to establish heart function cycles, the stimulator component will create a train of electrical pulses that are generated during the refractory period in the heart cycle. More specifically, this train of electrical pulses will preferably have a pulse frequency that is less than 600 pulses per second, and will extend over a time duration in the heart cycle that is less than approximately 300 ms. Also, the intensity of the pulses in this pulse train will be less than the level that would be effective for directly stimulating a heart muscle contraction. Structurally, the voltage source (pacemaker) and the stimulator can be electrically connected with the electrode by a same wire.

For an operation of the present invention, an appropriate sympathetic nerve (nerve bundle) on the epicardial surface of the left ventricle is identified. Importantly, the nerve needs to be located either adjacent the coronary sinus or a vein that is connected to the coronary sinus. Location of this nerve can be accomplished by well known mapping techniques, such as by using a loop catheter. Once the site of an appropriate sympathetic nerve has been identified, the electrode is advanced through the venous system to be positioned at the site adjacent to the nerve in the vein. The electrode can then be activated.

Activation of the electrode can be accomplished either actively, in accordance with pre-programmed instructions from the computer, or reactively in response to the contractions of the heart muscle. In either case, an activation of the electrode is done twice during each heart cycle, for two different reasons. For one, the electrode is activated to cause contractions of the heart muscle at the predetermined rate established for heart cycles by the voltage source. For another, within the refractory period of each heart cycle, a train of pulses is generated to stimulate the sympathetic nerve for a release of norepinephrine. Importantly, the sympathetic nerve should be stimulated while the heart muscle is not able to electrically respond to electrical stimuli. Nevertheless, the released norepinephrine is available for stimulation of the heart muscle when the heart is ready for its next contraction. Thus, stimulation of the sympathetic nerve only indirectly assists a heart muscle contraction. Further, the voltage level necessary for stimulating the sympathetic nerve is lower than the threshold necessary for a direct stimulation of the heart muscle.

An important feature of the present invention is that whenever a heart function cycle is interrupted (e.g. a premature contraction during diastole) the system will reset itself. Specifically, when competing electrical activity interrupts a heart cycle, the sensor will detect the competing activity, and will accordingly inhibit the voltage source output until a time interval is sensed wherein there is no competing electrical activity. At that time (i.e. when there is no longer any competing electrical activity), the voltage source (pacemaker) is returned to its normal operation. Thus, the system returns to the function of concertedly stimulating heart muscle contractions and the secretions of norepinephrine from a sympathetic nerve that will assist the heart muscle contractions.

A computer program for the present invention is required to coordinate and control the electrical stimulation functions of the voltage source and the stimulator. Specifically, in an operation of the present invention, the voltage source (pacemaker) may be used to activate an electrode that will directly stimulate contractions of the heart muscle at the predetermined rate for heart function cycles. Importantly, the intensity of these electrical stimulations is computer-controlled and must be sufficient to cause a heart muscle contraction. As envisioned for the present invention, however, the required intensity is mitigated due to the assist that is provided by the secretion of norepinephrine from a sympathetic nerve. For the present invention, these secretions of norepinephrine are stimulated by an activation of the electrode. Specifically, for this purpose, a train of electrical pulses are generated whose duration and intensity are both computer-controlled. Thus, both heart muscle contractions and sympathetic nerve secretions are concertedly controlled by the computer.

As envisioned for the present invention, and as implied above, the system of the present invention may operate in any of several modes. For one, the computer can be pre-programmed with low-intensity stimulation patterns. For another, the sensor can be used to identify when electrical activation of the heart muscle occurs, and can then activate the voltage source for stimulation of the nerve during the heart's refractory period. Still another mode would be to couple the system into a larger assembly for the execution of other stimulation plans.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENTS

Figure 1:
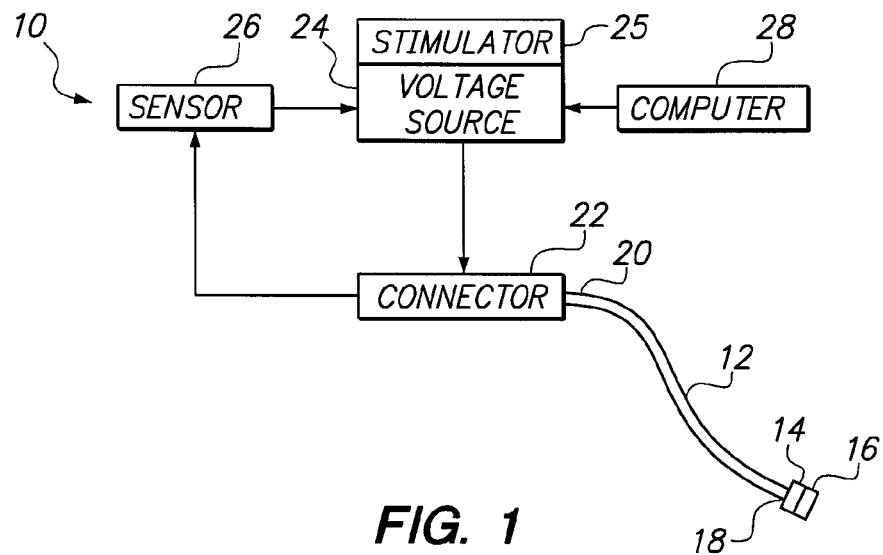
FIG. 1 is a schematic drawing of the components of a system for the present invention.

Referring initially to FIG. 1, a system for transvascular activation of sympathetic cardiac nerves that are useful for improving heart function in accordance with the present invention is shown and is generally designated 10. As shown, the system 10 includes a deployment catheter 12 having an electrical probe 14 and an electrode 16 mounted at its distal end 18. The proximal end 20 of the deployment catheter 12 is affixed to an electrical connector 22. As also shown in FIG. 1, the system 10 includes a voltage source 24 that is electrically connected to the connector 22. For purposes of the present invention, the voltage source 24 may be a pacemaker or a pacing catheter of a type well known in the pertinent art. Further, the voltage source 24 may include a stimulator 25 or, alternatively, the stimulator 25 may be an independent component. In either case, both the voltage source 24 and the stimulator 25 are electrically connected to the electrode 16.

Still referring to FIG. 1, it will be seen that the system 10 further includes a sensor 26 and a computer 28 that are each electrically connected to the voltage source 24. Also, the voltage source 24 is connected, through the connector 22, with the electrode 16 that is mounted at the distal end 18 of the deployment catheter 12. Further, the sensor 26 is connected with the probe 14 through the connector 22. With these connections, it is to be appreciated that the voltage source 24 is responsive to both the sensor 26 and to the computer 28.

Figure 2:
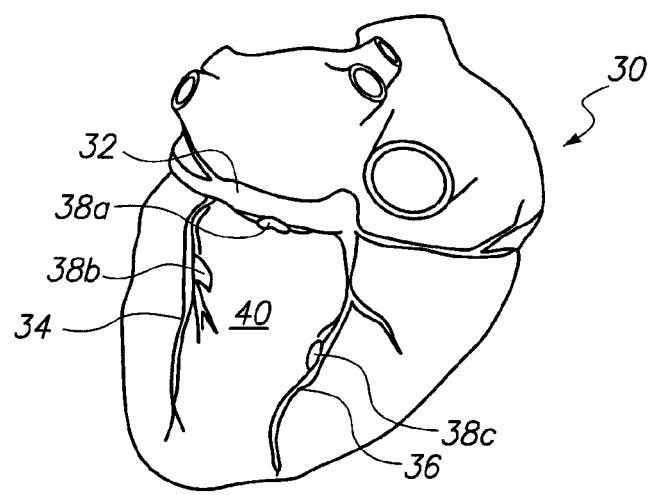
FIG. 2 is a drawing of the diaphragmatic surface of the heart showing only veins and proximate nerve bundles.

A heart muscle is shown in FIG. 2 and is generally designated 30. Anatomically, a view of the diaphragmatic surface of the heart muscle 30, (FIG. 2), shows its coronary sinus 32 and several connecting veins. In particular, the posterior vein 34 of the left ventricle, and the middle cardiac vein 36 are shown. Also shown are sympathetic nerve(s) 38 in the nervous system, of which the nerve bundles 38a, 38b and 38c are only exemplary. Importantly, the nerves 38 are located on the epicardial surface of the left ventricle 40, and they are adjacent to either the coronary sinus 32 or one of the veins connected with the coronary sinus 32 (e.g. veins 34 or 36).

For the operation of the system 10 of the present invention, the heart muscle 30 is initially mapped to identify an appropriate nerve(s) 38. Specifically, as implied above, an appropriate nerve 38 is one that is adjacent the coronary sinus 32 or a vein that is connected with the coronary sinus 32 (e.g. vein 34 or 36). Also, it is important that the nerve 38 be at a location on the epicardial surface of the left ventricle 40 of heart muscle 30 where it will be efficacious for stimulating the heart muscle 30. Once an appropriate nerve(s) 38 has been identified, the deployment catheter 12 is advanced through the vasculature of the patient (not shown) to position the electrode 16 in the vein (e.g. 32, 34 or 36) for stimulation of the adjacent nerve (e.g. respectively 38a, 38b or 38c).

Figure 3:
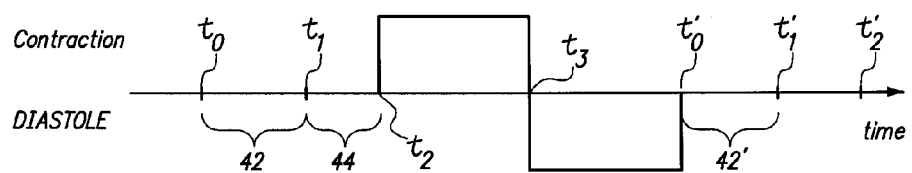
FIG. 3 is a time graph of the electrical and mechanical cycles of the heart.

FIG. 3 provides a generalized time graph for the cyclical activity of the heart muscle 30. More specifically, FIG. 3 provides a sequential time line for the interaction between the system 10 and the heart muscle 30 during a beat of the heart muscle 30. This includes, an electrical activation of system 10, the subsequent mechanical activation of the heart muscle 30 (i.e. contraction), and the subsequent relaxation or diastole that follows each contraction. The cycle, of course, is repetitive.

As shown for a single beat (i.e. cycle) of the heart muscle 30, activation of the heart muscle 30 begins at the time "$t_0$". This activation continues from the time "$t_0$" to the time "$t_1$", through what is known as the refractory period 42. In more detail, the refractory period 42 lasts for a time duration of about 120 to 300 ms, and occurs when the heart muscle 30 is not able to respond to an electrical stimulation. The nerve 38, however, is able to respond during a refractory period 42 by secreting norepinephrine. As envisioned for the system 10 of the present invention, the magnitude of the electric pulse that is provided by stimulator 25 for use in stimulating the nerve 38 during the refractory period 42 can be controlled. Specifically it can be programmed to be less than a level that would otherwise be efficacious for directly stimulating a contraction of the heart muscle 30.

At the time "$t_1$" shown in FIG. 3, the refractory period 42 ends and a relative refractory period 44 begins wherein the heart muscle 30 electrically recovers from the refractory period 42. The relative refractory period 44 then ends at the time "$t_2$" when the heart muscle 30 contracts. Importantly, this contraction is assisted by the norepinephrine that was secreted by nerve 38 in response to an activation of the voltage source 24 during the refractory period 42. As shown, this contraction is followed by a relaxation or diastole that lasts from a time "$t_3$" until another cycle begins at the time "$t_0$'". For purposes of the present invention, the computer 28 can be pre-programmed to accomplish the described cycle. Alternatively, the sensor 26 can receive a signal from the probe 14 that indicates a spontaneous electrical activation signal, and the voltage source 24 can then be responsive to the sensor 26 by activating the electrode 16 during the respective refractory period.

Figure 4:
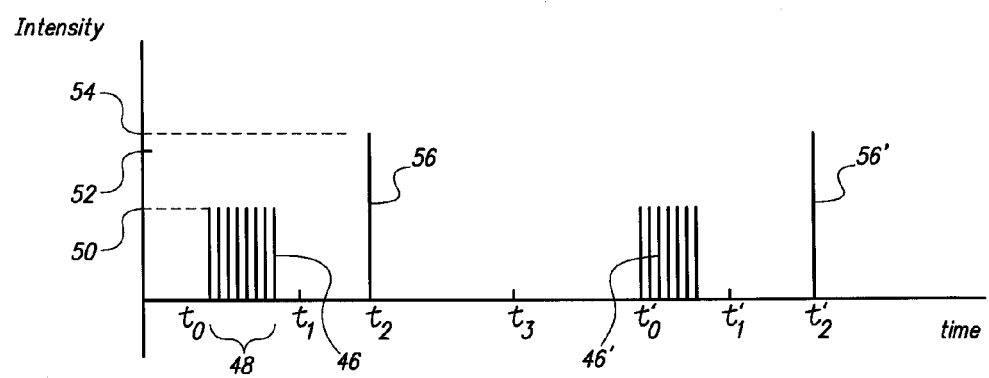
FIG. 4 is a time graph of electric pulse intensities provided for stimulating the heart muscle and a sympathetic nerve during a heart function cycle.

It is to be appreciated that the above disclosed operation of the stimulator 25 may be accomplished in concert with a direct stimulation of the heart muscle 30 by the voltage source 24. An example of this concerted operation is shown in FIG. 4, where a heart function cycle is shown to begin at a time "$t_0$" and extend to a time "$t_0$'". Note: primed identifiers in FIG. 4 pertain to a subsequent heart function cycle. For purposes of disclosure, it will be noted that a heart function cycle can also be considered as starting at the time "$t_2$" (when a heart contraction begins) and extending to a time "$t_2$'". In either case, if the heart muscle 30 is to be directly stimulated by the voltage source 24, this stimulation will be accomplished at a predetermined rate (e.g. 60/minute) to establish a desired duration for each heart function cycle.

With reference to FIG. 4, consider a heart function cycle that begins at time "$t_0$". Further, consider that a stimulation of a nerve bundle 38(a-c), and a stimulation of the heart muscle 30, will both occur during a same heart function cycle. As shown, a train of electrical pulses 46 is generated by the stimulator 25 during the refractory period 42 that extends from "$t_0$" to "$t_1$" (see FIG. 3). Within this refractory period 42, the pulse train 46 will continue through a time interval 48, and each pulse in the pulse train 46 will have an intensity 50 that is below the intensity 52 that is required for a direct stimulation of the heart muscle 30. As envisioned for the system 10 of the present invention, the time interval 48 will typically be less than 300 ms, and the frequency for electrical pulses in the pulse train 46 will be approximately 600/sec. Actual values for these variables are programmable, and will be controlled by the computer 28 during an operation of the system 10.

As noted above, several characteristics of the electrical pulses from the stimulator 25 are important for the present invention. For one, the magnitude and duration of each pulse can be pre-programmed and, thus, varied as required for the particular patient's needs. For another, the magnitude of each pulse should be and, indeed, is preferably below the voltage threshold that would otherwise be required to directly stimulate the heart muscle 30. With these considerations in mind, low-intensity stimulation patterns can be crafted to meet specific patient needs.

Still referring to FIG. 4, it will be seen that a stimulation of the heart muscle 30 can be programmed to occur, in concert with the stimulation of a nerve bundle (sympathetic nerve) 38(a-c), during a same heart function cycle. Of particular importance here is that the actual intensity 54 of a direct stimulation 56 at time "$t_2$" will be assisted by the consequences of pulse train 46. More specifically, the actual intensity 54 can be adjusted and set for subsequent control by the computer 28. This can be done with the understanding that secretions from nerve bundle 38(a-c), which result from pulse train 46, will assist stimulation 56 in stimulating the heart muscle 30. As envisioned for the system 10 of the present invention, operational parameters for both the pulse train 46 and the stimulation 56 can be programmed and controlled with the computer 28.

While the particular System and Method for Transvascular Activation of Cardiac Nerves With Automatic Restart as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A method for electrically stimulating a sympathetic nerve to improve heart function, the method comprising the steps of:

positioning an electrode on the epicardial surface of the heart in an epicardial vein adjacent the sympathetic nerves;

connecting a pacing device to the electrode to electrically activate contractions of the heart muscle at a predetermined rate for controlling a desired frequency of heart muscle cycles per minute, wherein each heart muscle electrical cycle includes a refractory period when heart muscle activation is effectively prevented, and a diastole when the heart is filling and excitable;

connecting a stimulator to the electrode in the epicardial vein to electrically stimulate the sympathetic nerves with a train of electric pulses for a specified time interval during the refractory period of the heart muscle cycle;

using the pacing device to monitor for premature contractions of the heart during diastole in the heart muscle electrical cycle to detect competing electrical activity that interrupts a heart cycle to inhibit electrical outputs; and resetting the start of a heart muscle electrical cycle upon sensing a premature contraction of the heart during the monitoring step by inhibiting a voltage output from the pacing device until a predetermined time interval is sensed in which there is no competing electrical activity.

2. A method as recited in claim 1 wherein each pulse in the train has a predetermined intensity below an intensity required for activating a contraction of the heart muscle.

3. A method as recited in claim 1 wherein the predetermined rate for heart muscle cycles and the specified time interval for the train of electric pulses within the refractory period of the heart muscle cycle are computer programmable.

4. A method as recited in claim 3 wherein the pulses in the train are generated at a frequency of less than 600 pulses per second.

5. A method as recited in claim 4 wherein the train of electric pulses continues for less than 300 ms.

6. A method as recited in claim 1 wherein accomplishment of the stimulating step, the monitoring step and the resetting step is coordinated by a computer program.

7. A method as recited in claim 1 wherein the pacing device and the stimulator use a same wire for respectively connecting with the electrode.

8. A method as recited in claim 1 wherein the pacing device is a pacemaker.

9. A method as recited in claim 1 wherein the predetermined rate for controlling the desired frequency of heart muscle cycles per minute is established to support a more synchronous activation of a cardiac pump function.

10. A system for electrically stimulating a sympathetic nerve to improve heart function which comprises:
    an electrode positioned on the epicardial surface of the heart adjacent the sympathetic nerve in an epicardial vein;
    a pacing device connected with the electrode to electrically activate contractions of the heart muscle at a predetermined rate for controlling a desired frequency of heart muscle cycles per minute, wherein each heart muscle cycle includes an electrical refractory period when heart muscle contraction is effectively prevented, and a diastole when the heart is filling;
    a stimulator connected with the electrode to electrically stimulate the sympathetic nerve with a train of electric pulses for a specified time interval during the refractory period of the heart muscle cycle;
    a sensor connected with the pacing device to monitor for premature contraction of the heart during diastole in the heart muscle electrical cycle to detect competing electrical activity that interrupts a heart cycle to inhibit electrical outputs; and
    a computer connected to the pacing device and to the stimulator for coordinating an operation of the pacing device and of the stimulator, and wherein the computer is responsive to the sensor for resetting the start of a heart muscle electrical cycle upon sensing a contraction of the heart during diastole step 1a inhibiting a voltage output from the pacing device until a predetermined time interval is sensed in which there is no competing electrical activity.

11. A system as recited in claim 10 wherein each pulse in the train has a predetermined intensity below an intensity required for activating a contraction of the heart muscle.

12. A system as recited in claim 10 wherein the predetermined rate for heart muscle cycles and the specified time interval for the train of electric pulses within the refractory period of the heart muscle cycle are computer programmable.

13. A system as recited in claim 12 wherein the pulses in the train are generated at a frequency of less than 600 pulses per second.

14. A system as recited in claim 13 wherein the train of electric pulses continues for less than 300 ms.

15. A system as recited in claim 10 wherein the pacing device and the stimulator use a same wire for respectively connecting with the electrode, and wherein the pacing device is a pacemaker.

16. A system for electrically stimulating a sympathetic nerve to improve heart function which comprises:
    a deployment catheter having a proximal end and a distal end;
    an electrode mounted on the distal end of the deployment catheter to be positioned at a site in the venous system of a patient adjacent to the sympathetic nerve, wherein the sympathetic nerve is located on an epicardial surface of the heart;
    a stimulator located at the proximal end of the deployment catheter, and connected to the electrode, for selectively transmitting a train of electrical pulses to activate the electrode and stimulate the sympathetic nerve during a refractory period in a diastole phase of a heart muscle cycle to release norepinephrine from the sympathetic nerve for improved heart muscle contraction; and
    a computer electronically connected to the stimulator for activating the electrode with the train of electrical pulses, in response to a contraction of the heart muscle, and in accordance with a pre-programmed low-intensity stimulation pattern.

17. A system as recited in claim 16 further comprising a pacing device located at the distal end of the deployment catheter and connected to the electrode for stimulating contractions of the heart muscle at a predetermined rate.

18. A system as recited in claim 17 further comprising:
    a probe mounted at the distal end of the deployment catheter for determining when the heart muscle experiences a contraction; and
    a sensor connected to the probe, and to the voltage source, for activating the electrode in response to a contraction of the heart muscle as determined by the probe.

19. A system as recited in claim 18 wherein the magnitude of each electric pulse is less than an effective level for directly stimulating a heart muscle contraction.

20. A system as recited in claim 19 wherein the pulses in the train are generated at a frequency of less than 600 pulses per second, and wherein the train of electric pulses continues for less than 300 ms.

* * * * *